United States Patent

Nagano et al.

[11] Patent Number: 4,599,104
[45] Date of Patent: Jul. 8, 1986

[54] HERBICIDAL PYRIDOTRIAZOLIUM COMPOUNDS

[75] Inventors: Eiki Nagano, Nishinomiya; Ryo Yoshida, Kawanishi, both of Japan

[73] Assignee: Sumitomo Chemical Company, Limited, Osaka, Japan

[21] Appl. No.: 577,969

[22] Filed: Feb. 8, 1984

[30] Foreign Application Priority Data

Feb. 15, 1983 [JP] Japan ................... 58-24333

[51] Int. Cl.⁴ ............... A01N 43/90; C07D 471/04
[52] U.S. Cl. .......................... 71/92; 534/770; 546/119
[58] Field of Search ................. 546/119; 71/92

[56] References Cited

U.S. PATENT DOCUMENTS 3,894,036  7/1975  Abu-el-Haj et al. ............. 260/295
3,939,174  2/1976  Abu-el-Haj et al. ............. 71/90 X
4,002,636  1/1977  Abu-el-Haj et al. ............. 71/92 X
4,437,877  3/1984  Nagano et al. ................. 71/90
4,452,981  6/1984  Nagano et al. ................. 544/236

Primary Examiner—Richard A. Schwartz
Attorney, Agent, or Firm—Birch, Stewart, Kolasch & Birch

[57] ABSTRACT

A pyridotriazolium compound of the formula:

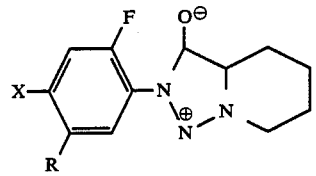

wherein R is a hydrogen atom, a $C_1$–$C_4$ alkoxy group, a $C_3$–$C_4$ alkynyloxy group, a $C_3$–$C_4$ alkenyloxy group or a $C_1$–$C_4$ alkylthio group and X is a chlorine atom or a bromine atom, which is useful as a herbicide.

20 Claims, No Drawings

HERBICIDAL PYRIDOTRIAZOLIUM COMPOUNDS

The present invention relates to pyridotriazolium compounds, and their production and use.

The said pyridotriazolium compound (hereinafter referred to as "pyridotriazolium(s)") are representable by the formula:

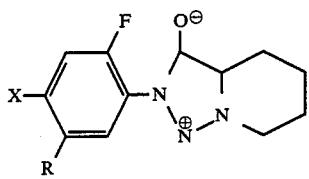

wherein R is a hydrogen atom, $C_1$-$C_4$ alkoxy group, a $C_3$-$C_4$ alkynyloxy group, a $C_3$-$C_4$ alkenyloxy group or a $C_1$-$C_4$ alkylthio group and X is a chlorine atom or a bromine atom.

Among the pyridotriazoliums (I) of the invention, favorable is 2-(4-chloro-2-fluoro-5-propargyloxyphenyl)-4,5,6,7-tetrahydro-[1,2-c]-1,2,3-pyridotriazolium-3-olate.

It is known that some pyridotriazoliums (I) exhibit a herbicidal activity. For instance, U.S. Pat. Nos. 3,939,174 and 4,002,636 disclose that 2-(2,4-dichlorophenyl)-4,5,6,7-tetrahydro-[1,2-c]-1,2,3-pyridotriazolium-3-olate, etc. are useful as herbicides.

It has now been found that the pyridotriazoliums (I) show a strong herbical activity against a wide variety of weeds including broad-leaved weeds, Graminaceous weeds and sedge weeds at small doses in agricultural plowed field and do not produce any material phytotoxicity on various agricultural crops (e.g. cotton).

Examples of broad-leaved weeds are wild buckwheat (*Polygonum convolvulus*), pale smartweed (*Polygonum lapathifolium*), common purslane (*Portulaca oleracea*), common lambsquarters (*Chenopodium album*), pigweed (*Amaranthus patulus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), wild carrot (*Daucus carota*), cleavers (*Galium aparine*), ivyleaf morningglory (*Ipomoea hederacea*), tal morningglory (*Ipomoea purpurea*), field bindweed (*Convolvulus arvensis*), red dead-nettle (*Lamium purpureum*), henbit (*Lamium amplexicaure*), jimsonweed (*Datura stramonium*), black nightshade (*Solanum nigrum*), birdseye speedwell (*Veronica persica*), ivyleaf speedwell (*Veronica hederaefolia*), cocklebur (*Xanthium strumarium*), sunflower (*Helianthus annuus*), scentless chamomile (*Matricaria inodola*), corn marigold (*Chrysanthemum segetum*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oat (*Avena sativa*), wild oat (*Avena fatua*), johnsongrass (*Sorghum halepense*), quackgrass (*Agropyron repens*), etc. Examples of sedge weeds are rice flatsedge (*Cyperus iria*), purple nutsedge (*Cyperus rotundus*), etc.

Likewise, the pyridotriazoliums (I) show a strong herbicidal activity at small doses against a wide variety of weeds including Graminaceous weeds (e.g. barnyardgrass (*Echinochloa oryzicola*)), broad-leaved weeds (e.g. false pimpernel (*Lindernia procumbens*), redstem (*Rotala indica*), waterwort (*Elatine triandra*)), sedge weeds (e.g. umbrella-plant (*Cyperus defformis*), hardstem bulrush (*Scirpus juncoides*), slender spikerush (*Eleocharis acicularis*), water nutgrass (*Cyperus serotinus*)) and pickerel-weed (*Monochoria vaginalis*) and arrowhead (*Sagittaria pygmaea*), etc. in paddy field. Particularly, the pyridotriazoliums (I) of the invention show a high selectivity to cotton by soil treatment.

The pyridotriazoliums (I) can be produced by reacting an aniline of the formula:

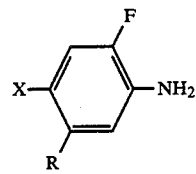

wherein X and R are each as defined above with nitrous acid in at least an equimolar proportion to give a benzodiazonium compound, reacting the benzodiazonium compound with pipecolinic acid in an inert solvent (e.g. water, dichloromethane) in the presence of a base (e.g. triethylamine, pyridine) at $-10°$ to $10°$ C. to give a triazene of the formula:

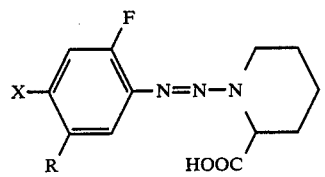

wherein X and R are each as defined above and reacting the triazene (III) with acetic anhydride-pyridine or thionyl-chloride-pyridine in at least an equimolar proportion at $0°$ to $-30°$ C. for dehydrative ring closure.

The starting aniline (II) is known (cf. EP No. 0061741A).

A practical and presently preferred embodiment for production of the pyridotriazoliums (I) is illustratively shown in the following Example.

EXAMPLE 1

4-Chloro-2-fluoro-5-methoxyaniline (2.3 g) was dissolved in conc. hydrochloric acid (7 ml) and water (30 ml), and a solution of sodium nitrate (1 g) in water (3 ml) was dropwise added thereto at $-10°$ to $0°$ C. The resultant mixture was stirred for 30 minutes, and then urea was added thereto until a negative result by a starch paper test was obtained. The mixture was then gradually added to a cooled solution of pipecolinic acid (1.7 g) and triethylamine (6 ml) in water (20 ml). The resulting mixture was stirred for one hour at $0°$ to $10°$ C. and extracted with dichloromethane. The extract was dried and evaporated in vacuo, and the residue was dissolved in ether (30 ml), followed by addition of acetic anhydride (3 ml) and pyridine (1.5 ml). The resultant mixture was allowed to stand at room temperature overnight, poured into ice-water and extracted with ethyl acetate. The extract was dried and evaporated in vacuo and the residue was purified by silica gel column chromatography with a mixture of ethyl acetate and ethanol (10:1) as an eluent to give 0.9 g of 2-(4-chloro-2-fluoro-5-methoxyphenyl)-4,5,6,7-tetrahydro-[1,2-c]-1,2,3-pyridotriazolium-3-olate (Compound No. 1). M.P. 161°–162.5° C.

Examples of the pyridotriazoliums (I) produced by the same procedure as above are shown in Table 1.

TABLE 1

| Compound No. | R | X | Physical constant |
|---|---|---|---|
| 1 | —OCH$_3$ | Cl | M.P. 161–162.5° C. |
| 2 | —OC$_3$H$_7$(iso) | Cl | M.P. 87–89° C. |
| 3 | —OCH$_2$C≡CH | Cl | M.P. 192–194° C. |
| 4 | H | Br | M.P. 177–178.5° C. |
| 5 | —SC$_4$H$_9$(sec) | Br | Glassy |
| 6 | —OCH$_2$CH=CH$_2$ | Cl | Glassy |

In the practical usage of the pyridotriazoliums (I), they may be formulated in any composition form such as emulsifiable concentrates, wettable powders, suspensions, granules, etc, in combination with a conventional solid or liquid carrier or diluent, a surface active agent or an auxiliary agent.

The concentration of the active ingredient in such composition is usually within a ragne of 0.05 to 95% by weight, preferably of 0.1 to 80% by weight.

Examples of the solid carrier or diluent are kaolin clay, attapulgite clay, bentonite, terra alba, pyrophyllite, talc, diatomaceous earth, calcite, walnut powders, urea, ammonium sulfate, synthetic hydrated silicon dioxide, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc.

The surface active agent used for emulsification, dispersion or spreading may be any of the anionic and nonionic type of agents. Examples of the surface active agent include alkylsulfates, alkylarysulfonates, dialkysulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esers, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts and % are by weight. The compound number of the active ingredient corresponds to the one in Table 1.

FORMULATION EXAMPLE 1

Fifty parts of Compound No. 2, 3 parts of calcium ligninsulfonate, 2 parts of sodium laurylsulfate and 45 parts of synthetic hydrated silicon dioxide are well mixed while being powdered to obtain a wettable powder.

FORMULATON EXAMPLE 2

Ten parts of Compound No. 3, 14 parts of polyoxyethylene styrylphenyl ether, 6 parts of calcium dodecylbenzenesulfonate and 70 parts of cyclohexanone are well mixed while being powdered to obtain an emulsifiable concentrate.

FORMULATION EXAMPLE 3

Two parts of Compound No. 1, 1 part of synthetic hydrated silicon dioxide, 2 parts of calcium ligninsulfonate, 30 parts of bentonite and 65 parts of kaolin clay are well mixed while being powdered. The mixture is then kneaded with water, granulated and dried to obtain a granule.

FORMULATION EXAMPLE 4

Twenty-five parts of Compound No. 4, 3 parts of polyoxyethylene sorbitan monooleate, 3 parts of carboxymethylcellulose and 69 parts of water are mixed and pulverized until the particle size of the powders becomes less than 5 microns to obtain a suspension.

The pyridotriazoliums (I) thus formulated in any suitable formualtion form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the pyridotriazoliums (I) over the top of the plants. It may also be applied directly to the weeds if care is taken to keep the chemical off the crop foliage.

The pyridotriazoliums (I) of the invention may be used together with other herbicides to improve their activity as herbicides, and in some cases, synergistic effect can be expected. Further, they may be applied in combination with insecticides, acaricides, nematocides, fungicides, plant growth regulators, fertilizers, soil improvers, etc.

The pyridotriazoliums (I) can be used as herbicides applicable to agricultural upland field as well as paddy field. They are also useful as herbicides to be employed for orchard, pasture land, lawn, forest, nonagricultural field, etc.

The dosage rate of the pyridotriazoliums (I) may vary on prevailing weather conditions, preparation used, prevailing season, mode of application, soil involved, crop and weed species, etc. Generally, however, the dosage rate is from 0.2 to 100 grams, preferably from 0.5 to 50 grams, of the active ingredient per are. The herbicidal composition of the invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), lignisulfonate, abiethylenic acid salt, dinaphthylmethanedisulfonate, paraffin, etc. The composition formulated in the form of granules may be normally applied as such without dilution.

The biological data of the pyridotriazoliums (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 2 below are used for comparison.

TABLE 2

| Compound No. | Chemical structure | Remarks |
|---|---|---|
| A | (structure with Cl, Cl, N, N, N⊕, O⊖, cyclohexane) | U.S. Pat. No. 3,939,174 |
| B | F₃C-phenyl-NHC(O)N(CH₃)₂ | Commercially available herbicide known as "fluometuron" (common name) |

TEST EXAMPLE 1

Plastic pots (diameter, 10 cm; height, 10 cm) were filled with upland field soil, and the seeds of Japanese millet, oat, tall morningglory and velvetleaf were sowed therein. A designed amount of the test compound formulated into an emulsifiable concentrate according to Formulation Example 2 and diluted with water was sprayed by means of a small hand sprayer at a spray volume of 10 liters per are, and then the soil was well mixed to the depth of 4 cm. The test plants were grown for 20 days in a greenhouse, and herbicidal activity was examined. The results are shown in Table 3.

TABLE 3

| Compound No. | Dosage (g/are) | Herbicidal activity | | | |
|---|---|---|---|---|---|
| | | Japanese millet | Oat | Tall morningglory | Velvetleaf |
| 1 | 20 | 5 | 5 | 5 | 5 |
| | 5 | 4 | 4 | 5 | 5 |
| 2 | 20 | 5 | 5 | 5 | 5 |
| | 5 | 5 | 5 | 5 | 5 |
| 3 | 20 | 5 | 5 | 5 | 5 |
| | 5 | 5 | 5 | 5 | 5 |
| 4 | 20 | 5 | 5 | 5 | 5 |
| A | 20 | 0 | 0 | 2 | 4 |

TEST EXAMPLE 2

Cylindrical plastic pots (diameter, 10 cm; height, 10 cm) were filled with upland field soil, and the seeds of Japanese millet, oat, radish and velvetleaf were sowed therein. Cultivation was carried out in a greenhouse for 10 days. A designed amount of the test compound formulated into an emulsifiable concentrate according to Formulation Example 2 and diluted with water containing a spreading agent was sprayed to the foliage of the test plants over the top by means of a small hand sprayer at a spray volume of 10 liters per are. Thereafter, the test plants were further grown for 20 days in the greenhouse, and herbicidal activity was examined. The results are shown in Table 4.

TABLE 4

| Compound No. | Dosage (g/are) | Herbicidal activity | | | |
|---|---|---|---|---|---|
| | | Japanese millet | Oat | Radish | Velvetleaf |
| 1 | 40 | 4 | 4 | 5 | 5 |
| 2 | 40 | 5 | 4 | 5 | 5 |
| 3 | 40 | 5 | 5 | 5 | 5 |
| | 10 | 5 | 4 | 5 | 5 |
| 4 | 40 | 5 | 4 | 5 | 5 |
| A | 40 | 1 | 0 | 2 | 4 |

TEST EXAMPLE 3

Cylindrical plastic pots (diameter, 8 cm; height, 12 cm) were filled with paddy field soil and seeds of barnyardgrass (*Echinochloa oryzicola*), three species of broad-leaved weeds, i.e. false pimpernel, redstem rotala, waterwort, and hardstem bulrush, were sowed in 1–2 cm depth. Water was poured therein to make a paddy field condition and rice seedlings at two-leaf stage were transplanted. The test plants were cultivated for 6 days in a greenhouse. Thereafter, a designed amount of the test compound formulated into an emulsifiable concentrate according to Formulation Example 2 and diluted with 5 ml of water was applied to the pots by perfusion. The test plants were further grown for 20 days in the greenhouse, and the herbicidal activity and the phytotoxicity were examined. The results are shown in Table 5.

TABLE 5

| Compound No. | Dosage (g/are) | Phytotoxicity Rice plant | Herbicidal activity | | |
|---|---|---|---|---|---|
| | | | Barnyardgrass | Broad-leaved weed | Hardstem bulrush |
| 1 | 10 | 1 | 5 | 5 | 5 |
| 2 | 2.5 | 1 | 4 | 5 | 5 |
| 3 | 2.5 | 1 | 5 | 5 | 4 |
| 4 | 10 | 1 | 5 | 5 | 3 |

TEST EXAMPLE 4

Vats (33×23×11 cm) were filled with upland field soil, and the seeds of hemp sesbania, sunflower, cocklebur, velvetleaf, tall morningglory, sickplepod, prickly sida, johnsongrass, green foxtail and large crabgrass were sowed therein and covered with soil in 1–2 cm depth. A designed amount of the test compound formulated into an emulsifiable concentrate according to Formulation Example 2 and diluted with water was sprayed to the soil surface by means of a small hand sprayer at a spray volume of 10 liters per are, and then the soil was well mixed to the depth of 4 cm. The seeds of cotton and soybean were sowed therein in 2 cm depth. The test plants were further grown for 20 days in a greenhouse, and the herbicidal activity and the phytotoxicity were examined. The results are shown in Table 6.

TABLE 6

| Compound No. | Dosage (g/are) | Phytotoxicity | | Herbicidal activity | | | | | | | |
|---|---|---|---|---|---|---|---|---|---|---|---|
| | | Cotton | Soybean | Hemp sesbania | Sunflower | Cocklebur | Velvetleaf | Tall morningglory | Sicklepod | Prickly sida | Johnson grass | Green foxtail | Large crabgrass |
| 1 | 5 | 1 | 2 | 4 | 4 | 5 | 5 | 5 | 5 | 5 | 5 | 5 | 5 |
| | 2.5 | 0 | 1 | 3 | 3 | 4 | 5 | 4 | 3 | 5 | 4 | 4 | 5 |

TABLE 6-continued

| Compound No. | Dosage (g/are) | Phytotoxicity | | Herbicidal activity | | | | | | | | | |
|---|---|---|---|---|---|---|---|---|---|---|---|---|---|
| | | Cotton | Soybean | Hemp sesbania | Sunflower | Cocklebur | Velvetleaf | Tall morningglory | Sickplepod | Prickly sida | Johnson grass | Green foxtail | Large crabgrass |
| 2 | 5 | 1 | 2 | 5 | 3 | 4 | 5 | 5 | 4 | 5 | 5 | 5 | 5 |
|   | 2.5 | 0 | 1 | 4 | — | 4 | 5 | 5 | 3 | 5 | 4 | 5 | 5 |
| 3 | 5 | 1 | — | 5 | 4 | 5 | 5 | 5 | 5 | 5 | 5 | 5 | 5 |
|   | 2.5 | 0 | — | 5 | 4 | 3 | 5 | 5 | 4 | 5 | 5 | 4 | 5 |
| B | 10 | 0 | 4 | 5 | 4 | 5 | 5 | 5 | 4 | 5 | 4 | 4 | 5 |
|   | 5 | 0 | 3 | 3 | 2 | 3 | 4 | 3 | 3 | 3 | 2 | 3 | 3 |

What is claimed is:

1. A compound of the formula:

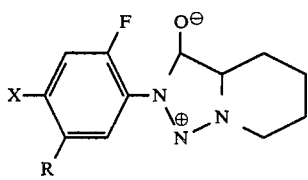

wherein R is a hydrogen atom, a $C_1$–$C_4$ alkoxy group, a $C_3$–$C_4$ alkynyloxy group, a $C_3$–$C_4$ alkenyloxy group or a $C_1$–$C_4$ alkylthio group and X is a chlorine atom or a bromine atom.

2. The compound according to claim 1, wherein R is a $C_1$–$C_4$ alkoxy group.

3. The compound according to claim 1, wherein R is a $C_3$–$C_4$ alkynyloxy group.

4. The compound according to claim 1, wherein R is a $C_3$–$C_4$ alkenyloxy group.

5. The compound according to claim 1, wherein R is a $C_1$–$C_4$ alkylthio group.

6. The compound according to claim 1, which is 2-(4-chloro-2-fluoro-5-propargyloxyphenyl)-4,5,6,7-tetrahydro-[1,2-c]-1,2,3-pyridothiazolium-3-olate.

7. The compound according to claim 1, which is 2-(4-chloro-2-fluoro-5-methoxyphenyl)-4,5,6,7-tetrahydro-[1,2-c]-1,2,3-pyridothiazolium-3-olate.

8. The compound according to claim 1, which is 2-(4-chloro-2-fluoro-5-isopropoxyphenyl)-4,5,6,7-tetrahydro-[1,2-c]-1,2,3-pyridothiazolium-3-olate.

9. The compound according to claim 1, which is 2-(4-chloro-2-fluoro-5-allyloxyphenyl)-4,5,6,7-tetrahydro-[1,2-c]-1,2,3-pyridothiazolium-3-olate.

10. A herbicidal composition which comprises as an active ingredient a herbicidally effective amount of the compound according to claim 1, and an insert carrier or diluent.

11. A method for controlling weeds which comprises applying a herbicidally effective amount of the compound according to claim 1 to the area where the weeds grow or will grow.

12. The method according to claim 11, wherein the area is a cotton field.

13. The method according to claim 11, wherein the application is made by a soil treatment.

14. A method for controlling the growth of weeds in a cotton field which comprises applying a herbicidally effective amount of the compound according to claim 2, to a cotton field where weeds grow or will grow.

15. A method for controlling the growth of weeds in a cotton field which comprises applying a herbicidally effective amount of the compound according to claim 7, to a cotton field where weeds grow or will grow.

16. A method for controlling the growth of weeds in a cotton field which comprises applying a herbicidally effective amount of the compound according to claim 8, to a cotton field where weeds grow or will grow.

17. A method for controlling the growth of weeds in a cotton field which comprises applying a herbicidally effective amount of the compound according to claim 3, to a cotton field where weeds grow or will grow.

18. A method for controlling the growth of weeds in a cotton field which comprises applying a herbicidally effective amount of the compound according to claim 4, to a cotton field where weeds grow or will grow.

19. A method for controlling the growth of weeds in a cotton field which comprises applying a herbicidally effective amount of the compound according to claim 9, to a cotton field where weeds grow or will grow.

20. A method for controlling the growth of weeds in a cotton field which comprises applying a herbicidally effective amount of the compound according to claim 5, to a cotton field where weeds grow or will grow.

* * * * *